US010197683B2

United States Patent
Aartsen

(10) Patent No.: US 10,197,683 B2
(45) Date of Patent: Feb. 5, 2019

(54) DIGITAL IRIS FOR CAMERA LENS ASSEMBLY

(71) Applicant: Adimec Advanced Image Systems b.v., Eindhoven (NL)

(72) Inventor: Reinder Gerrit Aartsen, Veldhoven (NL)

(73) Assignee: ADIMEC ADVANCED IMAGE SYSTEMS B.V., Eindhoven (NL)

( * ) Notice: Subject to any disclaimer, the term of this patent is extended or adjusted under 35 U.S.C. 154(b) by 225 days.

(21) Appl. No.: 15/191,636

(22) Filed: Jun. 24, 2016

(65) Prior Publication Data
US 2016/0377738 A1 Dec. 29, 2016

(30) Foreign Application Priority Data
Jun. 26, 2015 (NL) .................................. 2015037

(51) Int. Cl.
*H04N 5/243* (2006.01)
*G01T 1/17* (2006.01)
(Continued)

(52) U.S. Cl.
CPC .................. *G01T 1/17* (2013.01); *A61B 6/06* (2013.01); *A61B 6/4225* (2013.01); *A61B 6/487* (2013.01);
(Continued)

(58) Field of Classification Search
CPC ........ G01T 1/17; H04N 5/2254; H04N 5/374; H04N 5/238; H04N 5/243; H04N 5/32;
(Continued)

(56) References Cited

U.S. PATENT DOCUMENTS

| 4,918,534 A | 4/1990 | Lam et al. |
| 5,177,777 A * | 1/1993 | Niino ............... H04N 5/238 348/E5.04 |
| 2002/0032027 A1 | 3/2002 | Kirani et al. |

FOREIGN PATENT DOCUMENTS

| DE | 198 47 219 A1 | 5/1999 |
| JP | 2010269181 A | 12/2010 |

OTHER PUBLICATIONS

The Netherlands Search Report, dated Feb. 3, 2016, from corresponding NL Application.
(Continued)

*Primary Examiner* — Courtney Thomas
(74) *Attorney, Agent, or Firm* — Young & Thompson

(57) ABSTRACT

An imaging apparatus for an image intensifier (II) X-ray system includes a camera lens assembly (CLA) configured to cooperate with the II to create an X-ray image, the CLA including an image sensor and a lens. The image sensor is configured to convert received light and generate a digital image. The lens is configured to guide the light from the output surface to the image sensor, the lens having a fixed diaphragm. The CLA includes a diaphragm and/or neutral density filter with a fixed attenuation. A controller is configured to control an amount of amplification of the electric signals or the digital image. The sensor, e.g. CMOS sensor, is configured to amplify the analog electric signals before conversion into the digital image according to an analog gain, and the controller is configured to control the amount of amplification by controlling the analog gain applied by the image sensor.

13 Claims, 5 Drawing Sheets

(51) Int. Cl.
*A61B 6/00* (2006.01)
*H04N 5/238* (2006.01)
*H04N 5/32* (2006.01)
*A61B 6/06* (2006.01)
*H04N 5/225* (2006.01)
*H04N 5/374* (2011.01)

(52) U.S. Cl.
CPC ............ *A61B 6/542* (2013.01); *H04N 5/2254* (2013.01); *H04N 5/238* (2013.01); *H04N 5/243* (2013.01); *H04N 5/32* (2013.01); *H04N 5/374* (2013.01)

(58) Field of Classification Search
CPC ......... A61B 6/542; A61B 6/06; A61B 6/4225; A61B 6/487
See application file for complete search history.

(56) References Cited

OTHER PUBLICATIONS

Lomas, et al., "A high-resolution, two-dimensional, electron imaging integrated circuit", Measurement Science and Technology, vol. 9, No. 3, Mar. 1, 1998, pp. 391-398, XP20064439A, ISSN: 0957-0233, DOI:10.1088/0957-0233/9/3/012.

* cited by examiner

DIGITAL IRIS FOR CAMERA LENS ASSEMBLY

FIELD OF THE INVENTION

The invention relates to an imaging apparatus for an image intensifier X-ray system. More particularly, the invention relates to a Camera Lens Assembly (CLA) delivering digital imaging for Image Intensifier (II) based X-ray imaging systems.

BACKGROUND OF THE INVENTION

Existing X-ray imaging systems are known to use an image intensifier (II) to obtain an intensified visible image representing the X-rays detected at the detector side of the image intensifier. The visible image can be captured with a camera-lens assembly (CLA) resulting in a digital dataset that can be visualized on e.g. a display device and/or processed in many different ways. The digital datasets can be created and used for many purposes, including medical applications, machine vision, and non-destructive testing. The combination of the image intensifier and CLA is called IITV ('image intensifier-television camera').

An example CLA is the PEARL family of CLA's for digital IITV X-ray chains (Adimec Advanced Image Systems BV, Eindhoven, The Netherlands). This family of products comprises the PEARL-F for low dose fluoroscopy for e.g. universal radiography, and, amongst others, vascular applications, the PEARL-S for e.g. mobile C-arm systems (with image rotation) for surgery systems, and the PEARL-E for e.g. high dose exposure (spot imaging) and fluoroscopy for universal radiography and, amongst others, cardiovascular applications. The technique of fluoroscopy can be performed in a continuous X-ray mode, in which a low X-ray dose is generated continuously, or in a pulse X-ray mode, in which a sequence of X-ray pulses is generated. The CLA has a motorized iris and a Charge-Coupled Device (CCD) as the image sensor. This type of CLA can generate, for example, 1024×1024 pixels images with 12-bit pixels and has a dynamic range of 62 dB.

The amount of light that is produced by the image intensifier can vary depending on the X-ray dose. The known CLA has a motorized iris and/or a variable neutral density (ND) filter, to adapt to such differing brightness conditions. By varying the diaphragm and/or the ND filter, the dynamic range of the captured image is made as large as possible, while avoiding overexposure and/or clipping.

SUMMARY OF THE INVENTION

There is a need for an improved CLA. For example, it would be advantageous to have a CLA that is more cost effective or that is more reliable.

According to an aspect of the invention, an imaging apparatus for an image intensifier (II) X-ray system comprises a camera lens assembly (CLA) configured to cooperate with the II to create an X-ray image, the CLA comprising an image sensor and a lens, wherein the image sensor is configured to convert received light from an output surface of the II into analog electric signals and generate a digital image based on the electric signals, and wherein the lens is configured to guide the light from the output surface to the image sensor, the lens having a fixed diaphragm; and a controller configured to control an amount of amplification of the electric signals or the digital image.

The fixed diaphragm allows reduction of manufacturing cost. Further, less maintenance may be needed because of the absence of a motorized diaphragm. Further, the controlled amount of amplification of the analog electric signals or the controlled amount of amplification of the digital image (e.g., amplification amount of pixel values of the digital image), allow the imaging apparatus to be usable for a wide range of X-ray dose levels.

The CLA may have an optical path towards the image sensor, which optical path may have a fixed attenuation. This reduces cost because no adjustable components are necessary to adjust the attenuation. The image quality may still be realized by controlling the amount of amplification of the analog electric signals or the digital image. The output of the CLA may be more reproducible. The attenuation may be fixed in time. The attenuation refers to an attenuation of light passing through the optical path towards the sensitive portion of the image sensor.

The image sensor may be configured to amplify the analog electric signals in before conversion into the digital image according to a variable analog gain, and the controller may be configured to control the amount of amplification by controlling the analog gain applied by the image sensor. This allows the sensitivity of the image sensor to be adjusted to the amount of incoming light generated by the image intensifier. This way, the dynamic range of the CLA is increased without the use of a motorized iris.

The image sensor may be configured to generate the digital image with pixel values in a first range of digital values. The controller may comprise a digital gain unit for applying a digital amplification. The digital amplification involves mapping pixel values of the digital image from the first range of digital values onto a predetermined output range of pixel values according to a mapping. Herein, the controller is configured to control the amount of amplification by selecting the mapping according to the amount of amplification. This way, the subrange in which the pixel values of the digital image predominantly fall may be mapped to a fixed range, to generate an output image with a predictable intensity, even without a motorized iris.

The apparatus may further comprise an intensity determining unit for determining an intensity level of a sensed image. The controller may be configured to determine the amount of amplification based on the determined intensity of the sensed image. This is an efficient way to determine an appropriate gain level.

The controller may be configured to determine whether an intensity level of the sensed image is below a lower threshold, and if the intensity level of the sensed image is below the lower threshold, control the image sensor to increase the analog gain. This way, if the image intensity is low, the sensitivity of the sensor is increased using an analog gain. This way, the overall dynamic range of the CLA is improved.

The intensity level of the sensed image may be associated with an average intensity level of pixels of the sensed image. The controller may be configured to control the amount of amplification to map the average intensity level to a predetermined working point level. This way, a constant average intensity may be achieved at the working point, even without using a motorized iris.

The controller may be configured to apply digital amplification only when the analog gain is at a predetermined maximum level. If the average pixel values of the output image are below a predetermined working point, the analog gain may be increased first. If the working point is still not met when the analog gain is at a predetermined maximum value, the digital amplification may be applied. This way, the sensitivity and/or accuracy of the CLA is improved. However, this is not a limitation. In an alternative implementation, the controller may be configured to perform digital amplification first. In yet an alternative implementation, the controller may be configured to apply a combination of digital amplification and analog gain even if the analog gain is not at the predetermined maximum level. This may provide further flexibility.

The apparatus may further comprise a fixed filter to attenuate input light from the II passing through the diaphragm, wherein the fixed filter has a fixed attenuation, and wherein the attenuation of the filter corresponds to an attenuation necessary to attenuate input light having an intensity corresponding to a maximum supported II input X-ray dose intensity to a maximum supported image sensor input light intensity. The chosen attenuation of the filter may further be based on the given size of the fixed diaphragm. The filter may be a fixed filter configured to provide a fixed absorbance, regardless of the actual dose levels used. The filter allows more flexibility to choose the size of the fixed diaphragm. For example, the size of the fixed diaphragm may be adapted to the lens of the CLA to cause minimal reduction of image quality due to lens aberration, while keeping the diaphragm large enough to avoid diffraction. This way, image distortion is avoided while also avoiding overexposure of the sensor. The filter may be a neutral density filter, for example.

The image sensor may comprise a complementary metal oxide semiconductor (CMOS) image sensor. Such a sensor can be used for a large dynamic range. The image sensor may optionally have a dynamically configurable analog gain of electric signals generated in response to received light.

In a particular implementation example, the predetermined output range of pixel values includes at most 8 information bits. Surprisingly, the effective signal to noise ratio in low-dose applications such as fluoroscopy is often not more than 8 bits. In view of this, a dynamic range of 8 bits may be sufficient to accurately represent fluoroscopic images used in e.g. medical applications. This is because the noise included in the X-ray signals reaching the image intensifier causes the signal to have a relatively low signal to noise ratio.

The image intensity determining unit and/or the digital gain unit may be part of the CLA. Alternatively, these components can be part of e.g. an external workstation.

The apparatus may further comprise the image intensifier (II) configured to generate a fluoroscopic visible image on an output surface of the image intensifier when an input surface of the image intensifier is exposed to an X-ray dose, wherein the CLA is fixed to the II so that in operation the CLA captures an image of the output surface. The X-ray dose may be a continuous X-ray dose or a pulsed X-ray dose. Alternatively, the X-ray dose may be a single shot dose.

The apparatus may further comprise an X-ray source, and an X-ray controller configured to control the X-ray source to generate an X-ray dose at the detection surface within the predetermined supported II input X-ray dose intensity range.

The CLA may have a predetermined supported CLA input light intensity range corresponding to a predetermined supported II input X-ray dose intensity range. The attenuation of the optical path may be sufficiently large to prevent, during operation, overexposure of the image sensor as long as the input light intensity is smaller than or equal to a maximum CLA input light intensity of the supported CLA input light intensity range. This way, overexposure is avoided. The II input X-ray dose intensity range may be a specification of the II. The II converts an X-ray dose within the II input dose intensity range to a range of II output light intensities on the output screen of the II. This output light of the II becomes the input light of the CLA. The CLA input light intensity range thus corresponds to the II input X-ray dose intensity range and the II output light intensity range. The attenuation of the optical path may be sufficiently small to allow to pass, during operation, a number of imaging light photons to be collected by the image sensor greater than a number of X-ray photons collected by the photocathode of the II, over the range of supported II dose input levels. This way, the CLA does not reduce the signal to noise ratio noticeably.

According to another aspect of the invention, a method of X-ray imaging comprises guiding light received from an output surface of an image intensifier (II) to an image sensor of a camera lens assembly (CLA), by a lens having a fixed diaphragm;

converting the light into analog electric signals and generating a digital image based on the electric signals, by the image sensor; and controlling an amount of amplification of the analog electric signals or the digital image.

The person skilled in the art will understand that the features described above may be combined in any way deemed useful. Moreover, modifications and variations described in respect of the system may likewise be applied to the method, and modifications and variations described in respect of the method may likewise be applied to the system. Further, aspects of the invention may be implemented in form of a computer program product.

BRIEF DESCRIPTION OF THE DRAWINGS

In the following, aspects of the invention will be elucidated by means of examples, with reference to the drawings. The drawings are diagrammatic and may not be drawn to scale.

DETAILED DESCRIPTION OF THE INVENTION

Figure 1:
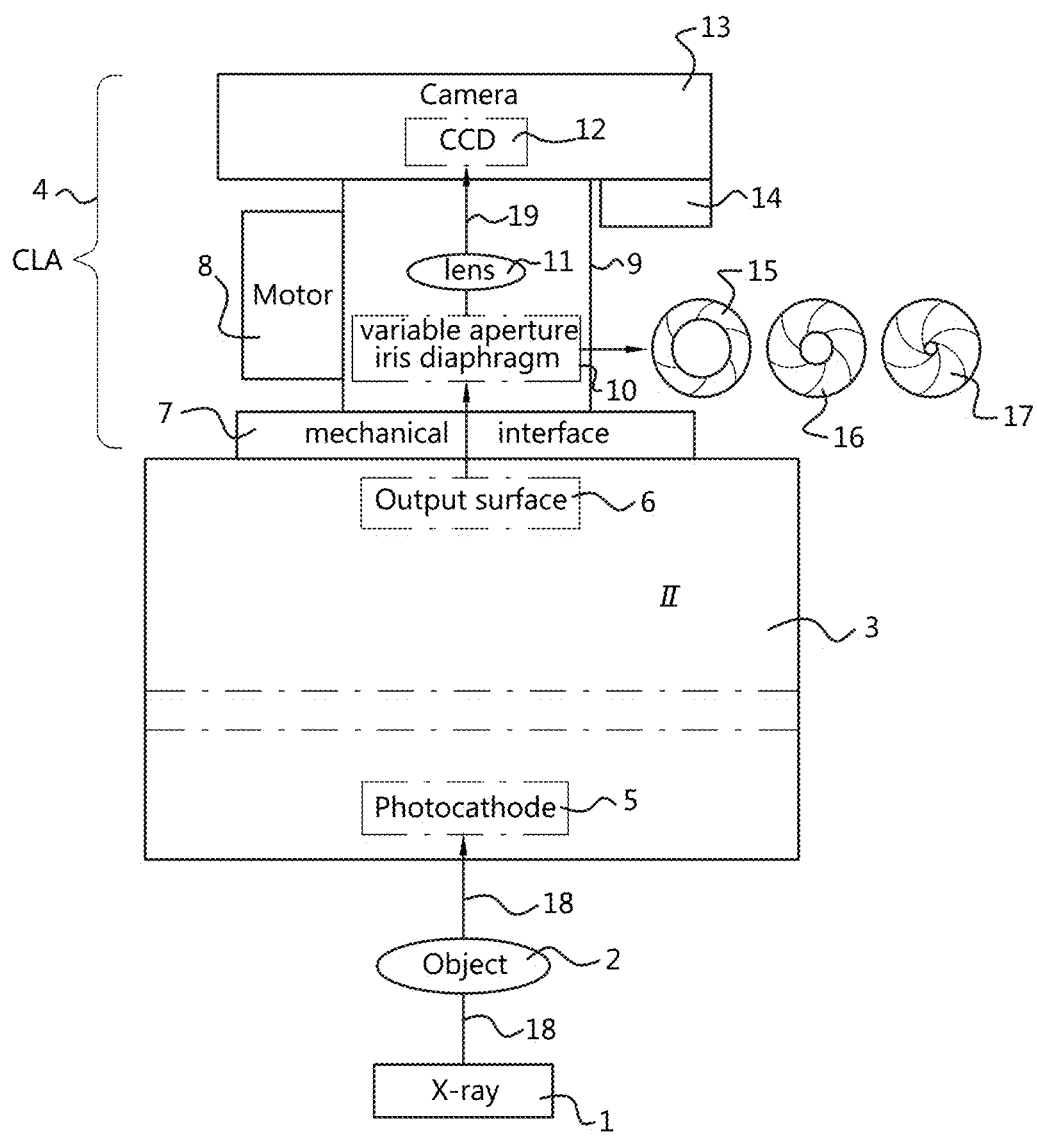
FIG. 1 is a block diagram of a prior art X-ray imaging system.

FIG. 1 illustrates a prior art X-ray imaging system. The system comprises an X-ray source 1 and an image intensifier (II) 3 having a photocathode 5 and an output window or output surface 6. The X-ray system further comprises a camera-lens assembly (CLA) 4. The CLA 4 comprises a mechanical interface 7 to fix the lens assembly 9 of the CLA 4 to the II 3. The CLA 4 further comprises a lens assembly 9, a motor 8, a camera 13, and a controller 14. The lens assembly 9 comprises a diaphragm 10 or iris. The aperture of the diaphragm 10 can vary, as illustrated by means of diaphragm states 15, 16, and 17. The aperture of the diaphragm 10 is controlled by the motor 8. The lens assembly 9 further comprises a lens 11. The camera 13 is fixed to the lens assembly 9. The camera 13 comprises a charge coupled device (CCD) as the image sensor and is configured to output digital images. In operation, an object 2 to be imaged is positioned in between the X-ray source 1 and the photocathode 5, and X-rays 18 produced by the X-ray source impinge on the photocathode 5 which generates light; the light is converted into an electron beam which is intensified and converted to light on output surface 6. The light 19 transmitted by the output surface 6 is received by the lens assembly 9, goes through the diaphragm 10 and lens 11 before it can reach the CCD 12 of the camera 13. The controller 14 controls the motor 8 either based on an external control signal or based on an analysis of the images output by the camera 13 or another light intensity measure.

Some prior art CLA's have a motorized neutral density filter with position feedback, to attenuate the incoming light depending on the overall light intensity.

Figure 3:
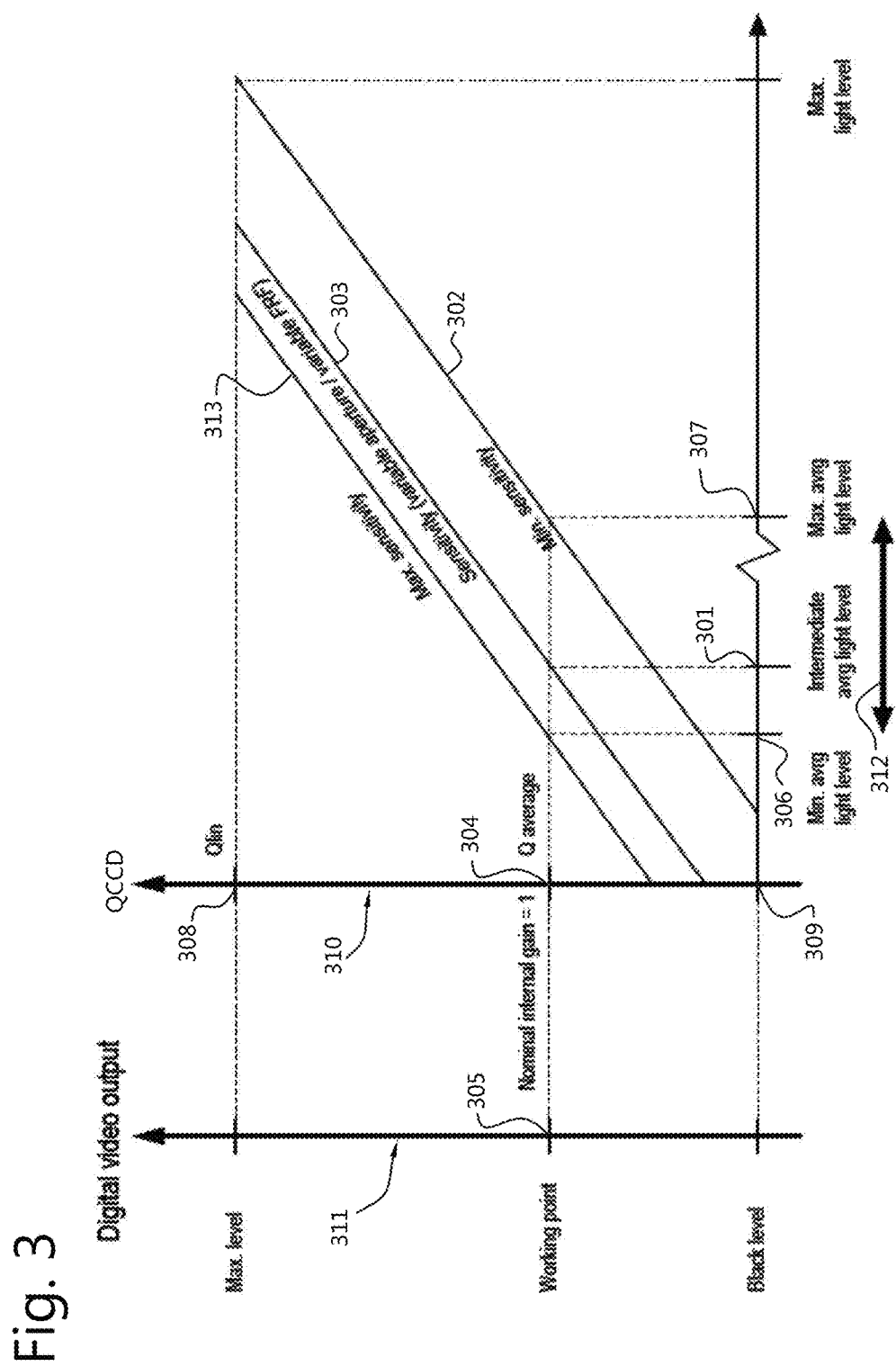
FIG. 3 is a graph illustrating response of the prior art X-ray imaging system.

FIG. 3 illustrates response behavior of the CLA. The horizontal axis represents the light intensity level of the light 19 reaching the variable aperture diaphragm 10. The vertical axis 310 represents the amount of light reaching the CCD 12. The vertical axis 311 represents the pixel values of the digital image generated by the CCD 12 and output by the CLA 4. Curve 303 indicates the relationship between light intensity reaching the diaphragm (horizontal axis) and light intensity reaching the CCD (vertical axis 310). Arrows 312 and curves 302 and 313 indicate that the curve 303 may be shifted by increasing or decreasing the aperture of the motorized iris. In most applications, the iris control by controller 14 is configured so that the iris is adjusted when the average light intensity level changes, so that the average light intensity reaching the CCD 12 is at a fixed level 304. The digital video output generated by the CCD 12 is output substantially unaltered, as indicated at vertical axis 311, with a nominal internal gain close to 1.

Figure 2:
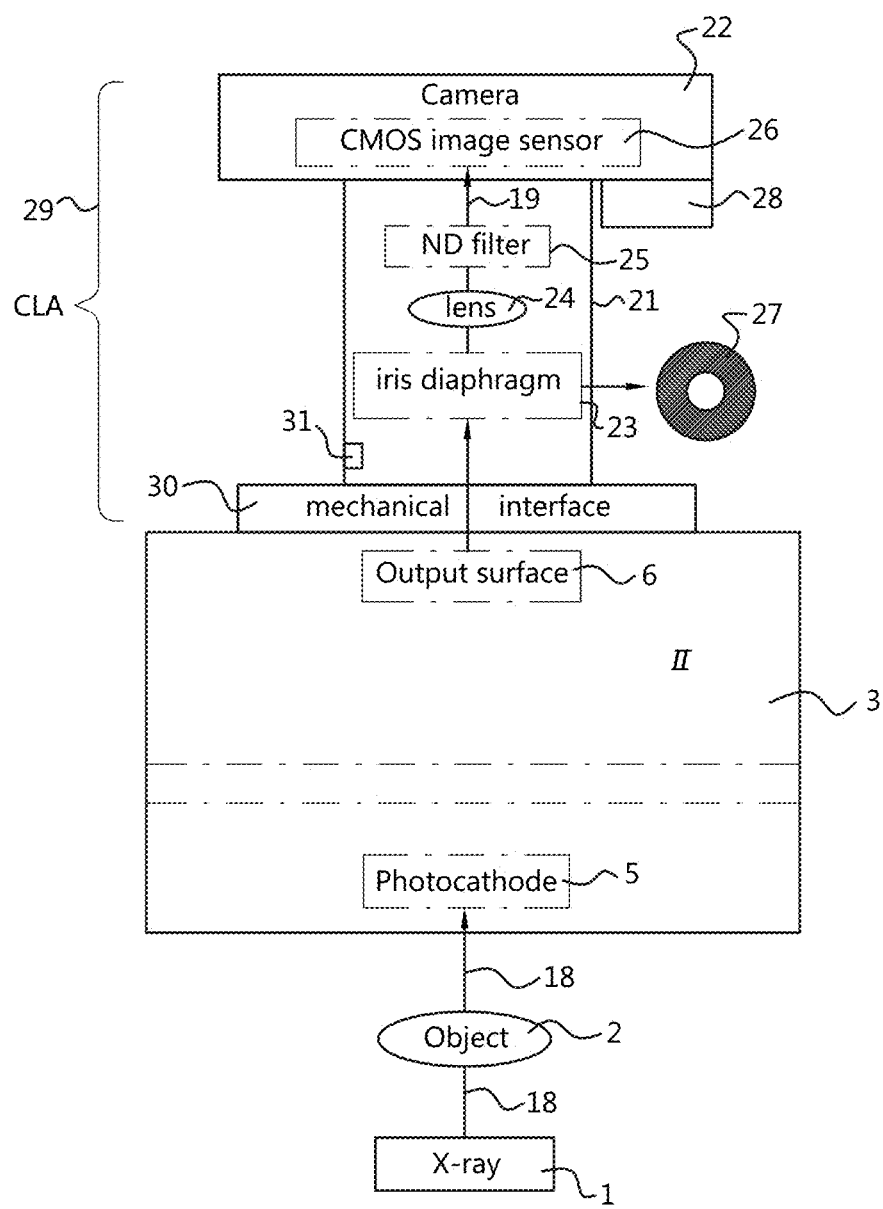
FIG. 2 is a block diagram of a an X-ray system with a fixed diaphragm according to an embodiment.

FIG. 2 illustrates an embodiment of the present invention. X-ray source 1, object 2, and II 3 with photocathode 5 and output surface 6 are similar to those of FIG. 1. Mechanical interface 30 of the CLA 29 allows to fix the lens assembly 21 of the CLA 29 to the II 3 to allow the light generated by the output surface 6 to pass through the diaphragm 23, lens 24, and optional filter 25 of the lens assembly 21 to reach the image sensor 26 of the camera 22 of the CLA 29. Controller 28 controls operation of the CLA 29. Diaphragm 23 has a fixed aperture, as illustrated by a single diaphragm state 27. Therefore, the CLA 29 does not have a motor to change the aperture of the diaphragm 23. Lens 24 can be the same type of lens or a different type of lens compared to lens 11 used in FIG. 1.

Filter 25 is optional and can be used to reduce the light intensity before the light 19 reaches the image sensor 26. For example, the filter 25 is a neutral density (ND) filter.

The image sensor 26 may comprise a CMOS image sensor, for example. However, other types of image sensors may also be used. Optionally, the image sensor 26 has a variable gain that can be controlled by controller 28.

Figure 4:
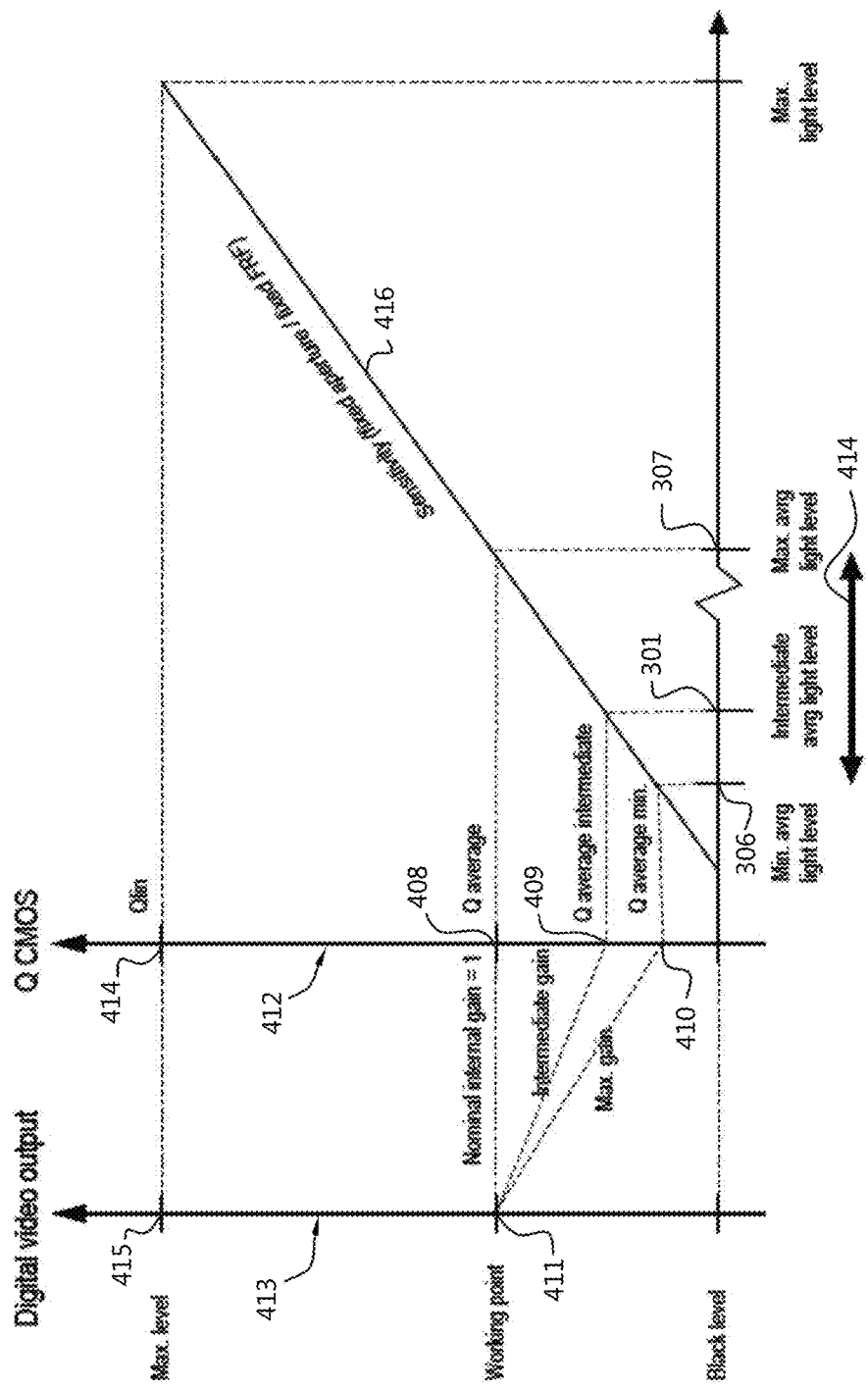
FIG. 4 is a graph illustrating response of an X-ray system according to an embodiment.

FIG. 4 illustrates response behavior of a CLA that has a diaphragm 23 with a fixed aperture 27. In FIG. 4, the horizontal axis represents light intensity of the light that reaches the lens assembly 21 from the output surface 6. The average light intensity of an image may vary, as illustrated by arrow 414 and different average light levels 301, 306, and 307. These averages represent the average light intensity of light rays produced by the output surface 6 at a given moment in time. The intensity of light entering the lens assembly 21 has a fixed relationship with the light intensity leaving the lens assembly 21 and impinging on the image sensor 26, because the diaphragm 23 is fixed. This relationship is represented by curve 416. Typically, during operation (e.g. during a fluoroscopy run) the average light flux varies between a minimum average light level 306 and a maximum average light level 307. Mostly, the actual average light level will be in between these two extremes, for example an intermediate average light level 301 may occur. These different influx light intensities 306, 301, 307 result in different average light intensities 410, 409, 408, respectively, impinging on the image sensor 26.

By proper amplification of the signals, a digital image can be realized in which the average image intensity is brought to a fixed (or otherwise predetermined) working point 411. That is, if the average influx light intensity corresponds to the working point 411, the internal gain of the image sensor can be set to 1. In FIG. 4, this occurs for the maximum influx intensity level 307, 408. When the average light intensity is lower, an internal gain greater than one can be set so that the lower average light intensity 301, 409 is mapped to the working point 411. The minimal supported average light intensity level 306, 410 is then determined by the maximal gain factor that can be provided.

It is noted that a similar amplification can also be performed in the digital domain, possibly by a processor separate of the image sensor, by applying an appropriate transformation to the digital pixel values of the digital image. For example, the pixel values can be multiplied by a multiplication factor corresponding to the desired gain factor. A nonlinear transformation of pixel values that maps the average pixel intensity to the working point while avoiding clipping is also possible. Such a transformation is known in the art per se. It is further noted that, when the average light intensity is above the working point 411, a gain factor smaller than one can be used in principle (not illustrated).

The analog amplification and digital amplification can be combined, so that a wider range of average input intensity levels can be supported.

Controller 28 is configured to control the analog and/or digital gain (or amount of amplification). To this end, controller 28 may have an input configured to receive a desired gain factor. Alternatively, controller 28 comprises an image analyzing module for determining the average pixel intensity of the digital image, and controls the gain to bring the average to the desired working point 411 based on a comparison of the determined average pixel intensity of the digital image and the desired working point. This comparison may involve determining a ratio of the two quantities to determine the gain factor. Alternatively, controller 28 may receive a signal indicative of a light intensity from a light intensity sensor 31, for example a photo-pickup, which can comprise an electro-optical subsystem comprising a photodiode.

In an implementation example, the image sensor 26 can amplify the detected signals up to a predetermined maximum gain factor $G_{max}$. When the controller 28 determines that a gain G is needed, and G is smaller than $G_{max}$, the controller controls the sensor 26 to apply the gain G. If the gain G is larger than $G_{max}$, the controller controls the sensor 26 to apply the gain $G_{max}$. To realize the desired gain G, a digital amplification of the digital image output by the image sensor 26 is performed by the controller. This digital amplification may use an amplification factor of $G/G_{max}$, so that the net gain factor of analog amplification and digital amplification is G. The digital amplification may be done by a multiplication by $G/G_{max}$, or by means of a nonlinear transformation that approximates the desired amplification, for example. Selecting the nonlinear transformation may involve selecting one or more parameters of the nonlinear transformation. Alternatively, a number of nonlinear transformations may be pre-computed in a look-up table, and one of the look-up tables may be selected based on the desired amount of amplification.

For example, the analog gain and/or the digital gain may be enabled by the controller when the intensity level of the sensed image is below a predetermined threshold value.

The intensity level may be expressed as an average intensity level. However, other measures of intensity are also possible, such as a sum of intensities, a median intensity, a minimum and maximum of an intensity range, and other ways to determine the intensity and to determine the desired intensity, the amount of amplification, and the mapping for digital amplification are possible.

A large diaphragm may cause any lens aberrations to become more apparent. Moreover, a small diaphragm may lead to diffraction to occur. The fixed size diaphragm and the lens may be selected so that lens aberrations do not occur (or are only limited) for the selected diaphragm size. Further, the diaphragm may be chosen large enough so that diffraction effect does not occur or is only limited. The effects of lens aberrations and diffraction may be measured by means of e.g. a point spread function. The image contrast and brightness may be controlled by the analog and digital gain, and by optional filter 25.

The CLA may support an input light intensity range corresponding to a predetermined supported II input X-ray dose intensity range. The input light intensity range may be part of a specification of the CLA, and the predetermined supported II input X-ray dose intensity range may be part of a specification of an image intensifier or of an II-CLA combination. The fixed diaphragm may be selected to have a size that is sufficiently small to prevent, during operation, overexposure of the image sensor when the input light intensity is smaller than or equal to a maximum CLA input light intensity of the supported CLA input light intensity range. Besides, it may be ensured that the size of the fixed diaphragm is sufficiently large to allow to pass, during operation, a number of imaging light photons to be collected by the image sensor (far) greater than a number of X-ray photons collected by the photocathode of the II, over the range of supported II dose input levels. This ensures that the X-ray dose is not wasted.

The image brightness may be further controlled by a filter. For example, a neutral density (ND) filter may be chosen so that the maximum influx light intensity is reduced to a level that has good results with the camera 22 and its sensor 26. The filter 25 may be a fixed filter. Alternatively, the filter may be removable or replaceable under control of the controller 28, depending on the influx light intensity.

The intensity of the sensed image may be determined by the controller by analyzing the digital image. Alternatively, a hardware light intensity sensor 31 may be used for the purpose. Such an optional hardware light intensity sensor may comprise a photodiode, for example.

The analyzing of the sensed image to determine the image intensity, as well as the computation of the desired amount of amplification and the separation of the total amount of amplification into analog amplification gain by the image sensor 26 and digital amplification gain may be performed by the controller 28. However, these tasks can also be performed by an external hardware unit, for example by a workstation connected to the controller 28 by means of a digital communication channel. Moreover, the digital images may be output to a display, storage media, and/or to an external hardware, such as a picture archiving and communications system.

Figure 5:
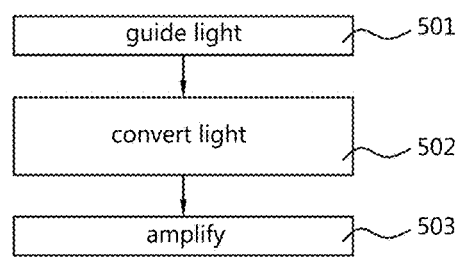
FIG. 5 is a flowchart of a method of generating an X-ray image.

FIG. 5 illustrates a method of X-ray imaging. Before starting the method, an X-ray source may be controlled to generate an X-ray beam and an image intensifier (II) may be controlled to receive the X-ray beam and to produce an II image on an output surface. Next, in step 501, light received from an output surface of the image intensifier (II) is guided onto an image sensor, by a lens having a fixed diaphragm. In step 502, the light is converted into analog electric signals, by the image sensor, and a digital image is generated based on the electric signals, by the image sensor. As set forth hereinabove, the CLA comprises the image sensor and the lens. The lens guides the light from the output surface onto a detection surface of the image sensor, and the lens has a fixed diaphragm and optionally a fixed ND filter or another type of fixed filter. Any further components in an optical path from the II output surface to the image sensor may be fixed and made of a material with a fixed attenuation. In step 503, an amplification of the electric signals or the digital image is controlled by a controller. The actual amplification may be performed by the image sensor, the controller, or another hardware component, under control of the controller.

In a particular example, a Camera Lens Assembly (CLA) is configured to deliver digital imaging for Image Intensifier (II) based medical X-ray, in particular fluoroscopy, imaging systems. The system, including II, can be of various brands. It is desirable to capture highly uniform and high contrast images at low patient X-ray dose in an economically sound way. The CLA can be equipped with a 'digital iris' in combination with a state of the art low noise high Dynamic Range (DR) global shutter Complementary Metal Oxide Semiconductor (CMOS) imaging sensor.

The 'digital iris' makes use of the significantly higher DR and the analog gain which may be available in some types of CMOS image sensors. The analog gain allows increasing the Signal to Noise Ratio (SNR), resulting in an even more extended overall DR.

'Digital iris' may employ analog gain generated by the CMOS image sensor, digital gain, or a combination thereof. In a particular implementation, digital gain is only applied on those occasions that analog gain turns out to be insufficient to achieve the desired level of gain.

In fluoroscopy applications, a continuous stream of X-ray images is generated, wherein the applied X-ray dose is relatively low. The X-ray shot noise in these applications is relatively high; the corresponding dynamic range is relatively narrow. In view of this, the signal to noise ratio (SNR) of the imaging system described herein can be made relatively low, typically 20 dB or less, because of the relatively low dose level encountered in these types of applications. For this reason, in some implementations, it is expected that a video output resolution of the camera as part of the CLA of 8 bit suffices. Such a video output resolution would correspond to a 48 dB dynamic range. It is a prerequisite in medical X-ray applications that the SNR of the imaging system is determined by the combination of X-ray signal and noise, predominantly shot noise, at the input side of the II. That is, the SNR of the imaging system should not be noticeably lower than the shot noise at the II. To ensure this, the imaging chain is configured such that the imaging light photons collected by the image sensor as part of the CLA outnumber by far the X-ray photons collected by the photocathode as part of the II. From calculations and observations during the design phase it may be ensured that this condition holds. The optical attenuation by means of the diaphragm in combination with an optional filter may be determined once for a specific type of II, with the criterion of avoiding saturation of the image sensor. By means of above-mentioned calculations it was found that, in this case, the X-ray shot noise remains the dominant source of noise over the whole X-ray dose range, in particular in the case of fluoroscopy.

For the X-ray dose ranges encountered in these types of applications and given a particular video output resolution in terms of bits per pixel, the average video level corresponding with the X-ray dose per image is called a working point. Typically, the working point corresponds to about ⅛ of the highest available pixel value in the output images of the CLA. However, the working point may be different depending on the application.

In case of a motorized iris in a prior art CLA, the maximum diaphragm of the lens is typically selected such that the working point is met at the lowest average X-ray dose level per image encountered in the applications for which the CLA is designed. At higher average X-ray doses per image the diaphragm is reduced by operating the motorized iris. This reduces the light flux impinging on the image sensor by a factor corresponding to the diaphragm. This factor is called the Flux Reduction Factor (FRF). The minimum diaphragm to be achieved by the motorized iris, and the corresponding maximum FRF, depends on the highest average X-ray dose level per image encountered in the applications for which the CLA is designed. The camera gain is typically fixed. Using the variable diaphragm, lens aberrations may occur when the diaphragm is large, and diffraction may occur when the diaphragm is small.

According to the techniques disclosed herein, the diaphragm of the lens may be selected such that the working point is met at the highest average X-ray dose per image encountered in the applications for which the CLA is designed. At lower average X-ray doses per image, the camera gain may be enhanced by enhancing the video output level of the image sensor by the corresponding factor, a factor inversely proportional to the FRF of the prior art CLA. The maximum gain to be achieved by the 'digital iris', depends on the lowest average X-ray dose level per image encountered in these types of application. The lens diaphragm may be fixed.

The fixed diaphragm allows selecting the size of the lens diaphragm such that the effects of lens aberrations and diffraction are as small as possible, as an optimal compromise between the adverse impact of lens aberrations and diffraction on the image contrast, keeping the light flux impinging on the image sensor at the desired level. It is possible to combine the fixed diaphragm with a filter such as a Neutral Density (ND) filter or a color filter in the lens as part of the CLA. The filter may be selected to attenuate the incoming light such that the working point is met at the highest average X-ray dose per image encountered in the types of applications for which the CLA is designed. Because of the filter, the size of the fixed diaphragm may be selected independently of the envisaged maximum supported image intensity.

Since the 'digital iris' does not have a motorized iris, it also does not need a dedicated controller to control the motorized iris. The 'digital iris' can be operated, for example, via the command control of the camera as part of CLA.

The techniques disclosed herein allow to produce a low-cost CLA, because of reduced Bill Of Material. A significantly more reliable CLA can be produced because of enhanced Mean Time Between Failure (MTBF) thanks to increased reliability as there is no need for moving parts. A CLA with on average significantly improved image resolution and/or contrast can be produced, because the fixed lens diaphragm can be optimized for optimal contrast. A CLA can be produced which has improved image uniformity, in a sense that the radial falloff in image intensity will be less because of the reduced lens diaphragm. Moreover, the CLA can have improved repeatability, because more functions are implemented digitally. The CLA can also have a more compact outline. Also the CLA can be more power efficient and/or easier to install.

A typical implementation example is a CLA imaging, which can be continuous or pulsed (depending on the selected X-ray imaging mode), a 25 mm diameter II output window with 1024×1024 pixel image resolution and 30 fps frame speed. Other II output window sizes such as 20 mm and 35 mm can also be used.

In an implementation example, an interface from the CLA towards the fluoroscopy system comprises a mainstream digital interfacing, like GigE Vision, Camera Link or equivalent, with command control and triggering, plus power. Further, a mechanical interface may be provided to mount the CLA on the II. This mechanical interface can be a separate adapter dedicated for a particular brand and type of II.

Given a CMOS image sensor with dynamic range of 74 dB (corresponding with 12 bits) and an effective CLA output resolution of 8 bits (corresponding with 48 dB), it is possible to apply digital gain to emulate a diaphragm of up to an FRF of 16 maximum (corresponding with 24 dB and 4 bits). This FRF exceeds the FRF specified for mainstream CLA's for fluoroscopy applications. The CLA output resolution may be larger than the actual number of information bits contained in the image pixels, for example to support legacy image processing hardware and software.

When analog gain is used in addition to digital gain, the maximum adaptability of the dynamic range is further extended. For example, if the analog gain adds another bit, the combined analog gain and digital gain corresponds to an FRF of as high as 32 (corresponding with 30 dB and 5 bits). This level of FRF approaches that specified for the more high-end CLA's for fluoroscopy applications.

Presently, the DR of the CLA specified for these types of applications is often 58 dB (corresponding with 9.5 bits). However, it may be viable to reconsider this DR specified given a typical SNR for the imaging system of 20 dB. In case of a CLA output resolution of 9.5, the maximum range of the digital gain still corresponds with an FRF of 6 (corresponding with 15 dB and 2.5 bits).

In a particular example, the controller 28 may be configured to receive at least two successive digital images from the image sensor 26, and combine the at least two images to obtain a further digital image. For example, corresponding pixels of the at least two images may be added or averaged to obtain the further digital image. This way, the resolution and/or dynamic range of each pixel may be improved. For example, the image sensor may provide digital images at a rate of 60 frames per second, and the controller 26 may combine each pair of two successive digital images, to obtain an output rate of 30 frames per second. Such a frame rate of 60 frames per second may be implemented using a CMOS based image sensor, for example. The further image (which is based on at least two digital images generated by the image sensor) can be subjected to the digital amplification procedure set forth hereinabove. Further, the analog gain of the image sensor 26 can be controlled in the way set forth hereinabove, when using the procedure of combining at least two successive images.

Examples concerning a CLA for II based X-ray imaging systems, in particular fluoroscopy imaging systems, include the following.

1. Application of a 'digital iris' consisting of gain, analog of the CMOS image sensor, digital or a combination thereof, where digital gain is only applied is those occasions that analog gain turns out to be insufficient.

2. Application of low noise high DR global shutter CMOS imaging sensor.

3. Application of an ND filter allowing to select the optimal lens diaphragm as compromise between the adverse impact of lens aberrations and diffraction on the image contrast, keeping the light flux impinging on the image sensor at the required level.

In a particular example, a method of X-ray imaging can comprise causing an X-ray source to generate an X-ray beam and an image intensifier (II) to receive the X-ray beam and to produce an II image on an output surface, capturing the II image by a camera lens assembly (CLA) configured to cooperate with the II to create an X-ray image, the CLA comprising an image sensor and a lens, wherein the image sensor converts received light from an output surface of the II into analog electric signals and subsequently generates a digital image, and wherein the lens guides the light from the output surface to the image sensor, the lens having a fixed diaphragm; and controlling an amplification of the analog electric signals or the digital image.

Some or all aspects of the invention may be suitable for being implemented in form of software, in particular a computer program product. Such computer program product may comprise a storage media, such as a memory, on which the software is stored. Such a computer program may also comprise code for programming a field programmable gate array (FPGA) and/or microcontroller (MCU). Also, the computer program may be represented by a signal, such as an optic signal or an electro-magnetic signal, carried by a transmission medium such as an optic fiber cable or the air. The computer program may partly or entirely have the form of source code, object code, or pseudo code, suitable for being executed by a computer system. For example, the code may be executable by one or more processors and/or FPGA MCU.

The examples and embodiments described herein serve to illustrate rather than limit the invention. The person skilled in the art will be able to design alternative embodiments without departing from the scope of the claims. Reference signs placed in parentheses in the claims shall not be interpreted to limit the scope of the claims. Items described as separate entities in the claims or the description may be implemented as a single hardware or software item combining the features of the items described.

The invention claimed is:

1. An imaging apparatus for an image intensifier (II) X-ray system, comprising:
a camera lens assembly (CLA) configured to cooperate with an image intensifier (II) to create an X-ray image, the camera lens assembly (CLA) comprising a complementary metal oxide semiconductor (CMOS) image sensor and an optical path towards the image sensor, the optical path having a fixed attenuation, the optical path comprising a lens,
wherein the image sensor is configured to convert received light from an output surface of the image intensifier (II) into analog electric signals, amplify the analog electric signals before conversion into a digital image according to an analog gain, and generate the digital image based on the analog electric signals, and
wherein the lens is configured to guide the light from the output surface to the image sensor, the lens having a fixed diaphragm with a fixed aperture; and
a controller configured to control an amount of amplification of the analog electric signals by controlling the analog gain applied by the image sensor.

2. The apparatus of claim 1,
wherein the image sensor is configured to generate the digital image with pixel values in a first range of digital values, and
the controller comprises a digital gain unit for applying a digital amplification by mapping pixel values of the digital image from the first range of digital values onto a predetermined output range of pixel values according to a mapping, wherein the controller is configured to control the amount of amplification by selecting the mapping according to the amount of amplification.

3. The apparatus of claim 1,
further comprising an intensity determining unit for detecting an intensity level of a sensed image;
wherein the controller is configured to determine the amount of amplification based on the determined intensity of the sensed image.

4. The apparatus of claim 3, wherein the image intensity determining unit and/or the digital gain unit is part of the camera lens assembly (CLA).

5. The apparatus of claim 3, wherein,
the controller is configured to:
determine whether an intensity level of the sensed image is below a lower threshold, and
when the intensity level of the sensed image is below the lower threshold, control the image sensor to increase the analog gain.

6. The apparatus of claim 3, wherein the intensity level of the sensed image is associated with an average intensity level of pixels of the sensed image, and the controller is configured to control the amount of amplification to map the average intensity level to a predetermined working point level.

7. The apparatus of claim 2,
wherein the controller is configured to apply digital amplification only when the analog gain is at a predetermined maximum level.

8. The apparatus of claim 1,
wherein the apparatus further comprises a fixed filter to attenuate input light from the image intensifier (II) passing through the diaphragm, wherein the fixed filter has a fixed attenuation, and wherein the attenuation of the filter corresponds to an attenuation to attenuate input light having an intensity corresponding to a maximum supported image intensifier (II) input X-ray dose intensity to a maximum supported image sensor input light intensity.

9. The apparatus of claim 2, wherein the image intensity determining unit and/or the digital gain unit is part of the camera lens assembly (CLA).

10. The apparatus of claim 1, further comprising the image intensifier (II) configured to generate a fluoroscopic visible image on an output surface of the image intensifier when an input surface of the image intensifier is exposed to an X-ray dose, wherein the camera lens assembly (CLA) is fixed to the image intensifier (II) so that in operation the camera lens assembly (CLA) captures an image of the output surface.

11. The apparatus of claim 10, further comprising an X-ray source, and an X-ray controller configured to control the X-ray source to generate an X-ray dose at the input surface within a predetermined supported image intensifier (II) input X-ray dose intensity range.

12. The apparatus of claim 1, wherein the camera lens assembly (CLA) has a predetermined supported camera lens assembly (CLA) input light intensity range corresponding to a predetermined supported image intensifier (II) input X-ray dose intensity range, wherein the fixed attenuation of the optical path is sufficiently large to prevent, during operation, overexposure of the image sensor when the input light intensity is smaller than or equal to a maximum camera lens assembly (CLA) input light intensity of the supported camera lens assembly (CLA) input light intensity range, and wherein the attenuation is sufficiently small to allow to pass, during operation, a number of imaging light photons to be collected by the image sensor greater than a number of X-ray photons collected by the photocathode or input surface of the image intensifier (II), over the supported image intensifier (II) input X-ray dose intensity range.

13. A method of X-ray imaging, comprising
guiding light received from an output surface of an image intensifier (II) to a complementary metal oxide semiconductor (CMOS) image sensor of a camera lens assembly (CLA), by an optical path towards the image sensor, the optical path having a fixed attenuation, the optical path comprising a lens having a fixed diaphragm with a fixed aperture;
converting the light into analog electric signals, amplifying the analog electric signals before conversion into a digital image according to an analog gain, and generating the digital image based on the analog electric signals, by the image sensor; and
controlling an amount of amplification of the analog electric signals by controlling the analog gain applied by the image sensor.

* * * * *